United States Patent [19]
Villuendas Yuste et al.

[11] Patent Number: 5,245,410
[45] Date of Patent: Sep. 14, 1993

[54] OPTICAL FIBER SENSOR BASED ON THE EXCITATION OF SURFACE PLASMON

[75] Inventors: Francisco Villuendas Yuste; Francisco Javier Pelayo Zueco, both of Zaragoza, Spain

[73] Assignee: Cables De Communicaciones S.A., Zaragoza, Spain

[21] Appl. No.: 553,877

[22] Filed: Jul. 16, 1990

[30] Foreign Application Priority Data

Jul. 25, 1989 [ES] Spain .................................. 8902630

[51] Int. Cl.$^5$ ............................................. G01N 21/55
[52] U.S. Cl. .................................................... 356/445
[58] Field of Search .............................. 356/445–448, 356/244; 250/227.25, 341; 422/82.06, 82.07, 82.11

[56] References Cited

U.S. PATENT DOCUMENTS

4,844,613  7/1989  Batchelder et al. ............... 356/445
4,889,427  12/1989  Van Veen et al. ................. 356/445

OTHER PUBLICATIONS

Nylander et al, "Gas Detection by Means of Surface Plasmon Resonance", Sensors and Actuators, vol. 3, pp. 79–88, 1983.
Liedberg et al, "Surface Plasmon Resonance for Gas Detection and Biosensing," Sensors and Actuators, vol. 4, pp. 299–304, 1983.
Koki Matsubara et al., Applied Optics, Mar. 15, 1988, vol. 27, No. 6, pp. 1160–1163.
L-M. Zhang, et al., Electronics Letters, Nov. 10, 1988, vol. 24, No. 23, pp. 1469–1470.
M. Matsubara et al., Applied Spectroscopy, 1988, vol. 42, No. 8, pp. 1375–1379.

Primary Examiner—Vincent P. McGraw
Assistant Examiner—K. P. Hantis
Attorney, Agent, or Firm—Darby & Darby

[57] ABSTRACT

Optical fiber sensor in an external medium based on the excitation of surface plasmon comprised of a sensor head formed by a transparent body having a first flat surface provided with a thin metal layer on which the optical excitation of the surface plasmon is produced. A mirrored surface positioned perpendicular to the first flat surface and a second flat surface forming an angle Φ determined by the refractive indexes of the transparent body and of the external medium. The sensor emitting light to the transparent body and detecting light from the transparent body, whereby variations of the optical properties of the sensor are determined.

13 Claims, 4 Drawing Sheets

OPTICAL FIBER SENSOR BASED ON THE EXCITATION OF SURFACE PLASMON

OBJECT OF THE INVENTION

As is expressed in the title of the present specification, the following invention consists of an optical fiber sensor based on the excitation of surface plasmon, which is useful for use in chemical detection, biochemical analysis, etc.

The device is based on the resonant optical excitation of surface plasmon on the interface existing between a thin metal film and a controlled outer dielectric medium.

The object of the patent is to effect a small portable sensor device, without any moveable pieces and which by means of optical fibers permits centralized remote control thereof.

BACKGROUND OF THE INVENTION

Surface plasmon or SPO (Surface plasmon Oscillation) are confined electromagnetic waves which are propagated in the interface existing between a metal medium and another dielectric one. Optical excitation of a flat surface can only take place when polarization light p incides, in total reflection conditions, on said surface. Besides, the resonant coupling of energy between the incident beam and the surface plasmon is produced when the component parallel to the metal-dielectric interface of the wave vector of the evanescent field, Ken sen $\theta$, where $\theta$ is the incidence angle, approaches the wave vector of the plasmon $K_{sp}$. In a structure with three different media, i.e., a dielectric, a metal film and an external medium (i.e., the medium upon which the measurement is made), the plasmon vector Ksp is given by the complex value that verifies the following equation.

$$[V_1 n_2^2 + V_2 n_1^2] \cdot [V_1 n_o^2 + V_o n_1^2] +$$
$$[V_1 n_o^2 - V_o n_1^2] \cdot [V_2 n_1^2 - V_1 n_2^2] \cdot$$
$$\exp(-2 V_1 d) = 0$$

when $$V_0 = \left[ K_{sp}^2 - \frac{n_0^2 w^2}{c^2} \right]^{\frac{1}{2}}$$

$$V_1 = \left[ K_{sp}^2 - \frac{n_1^2 w^2}{c^2} \right]^{\frac{1}{2}}$$

$$V_2 = \left[ K_{sp}^2 - \frac{n_2^2 w^2}{c^2} \right]^{\frac{1}{2}}$$

with $Re(V_j) > 0$ and if $Re(V_j) = 0$ then $Im(V_j) < 0$; w is the optical frequency, c is the speed of the light, d is the thickness of the metal layer and $n_0$, $n_1$ and $n_2$ are the refractive indexes of the first dielectric medium of the metal layer and of the outer medium, respectively. Consequently, the wave vector of the plasmon, which depends on the refraction indexes of the three medium in contact, determines the incidence angle for which the resonant optical excitation is given. For this angle the reflection coefficient given by $$r = \frac{r_{o1} + r_{12}e^{-2u_1 d}}{1 + r_{o1}r_{o2}e^{-2u_1 d}}$$

with $r_{o1} = \frac{u_o n_1^2 - u_1 n_o^2}{u_o n_1^2 + u_1 n_o^2}$ and $r_{12} = \frac{u_1 n_2^2 - u_2 n_1^2}{u_1 n_2^2 + u_2 n_1^2}$ where $$u_o = \left[ (K sen\theta)^2 - \frac{n_o^2 w^2}{c^2} \right]^{\frac{1}{2}}$$

$$u_j = \left[ (K sen\theta)^2 - \frac{n_1^2 w^2}{c^2} \right]^{\frac{1}{2}}$$

$$u_2 = \left[ (K sen\theta)^2 - \frac{n_2^2 w^2}{c^2} \right]^{\frac{1}{2}}$$

has an abrupt minimum, which is a function of the incidence angle, as well as of the refraction indexes and, particularly, of the refraction index of the outer medium.

Different types of sensors based on the excitation of surface plasmon have been described in literature, but always with discrete optical elements and using the angle at which the maximum attentuation of the reflexion coefficient is produced as the measure parameter.

Thus, for this purpose, C. Nylander, B. Liedberg and T. Lindt, Sens. § Actuators, vol 4 p. 299, 1983, use angular sweep of the detector, K. Matsubara, S. Kawata and S. Minami, Appl. Dpt., vol. 27, p. 1160, 1988, use a multiple linear detector and L. M. Zhang and D. Uttamchandani, Electron. Lett., vol. 24, p. 1469, 1988, make a sweep in wave length. Such devices require very precise instruments or else a complicated elaboration of the data obtained, aside from having inconveniences derived from the geometric shape; this makes these devices not portable and difficult to use in industrial fields. On the other hand, these devices do not have the possibility of optical connection for communication with centralized remote control units.

DESCRIPTION OF THE INVENTION

The device consists of a sensor head, a light emission and detection system and an optical fiber system that connects the sensor head to the light emission and detection systems. The sensor head consists of a transparent geometric figure, in which one of its surfaces is a cylindric mirror, whose axis is in the plane of said geometric figure; upon one flat surface perpendicular to the cylindric mirror, a flat parallel sheet of a transparent material similar to the one that geometric figure is made out of, and upon which a thin metal layer has been deposited is adhered by means of a refractive index adapter liquid (for example, for BK7 glass, D.P.X. "8711" adapter of DIFCO, N=1.532.) The optical excitation of surface plasmon is produced on this metal layer; and a third one, forming an $\Phi$ angle determined by the refractive indexes of the medium constituting the transparent geometric figure and the outer medium.

The end of the incident optical fiber is situated in the axis of the cylindric mirror, in such a way that the image of the end of the fiber through the metal film and the cylindric mirror is an interval of the axis itself of the cylinder. In a point of this interval, the end of the detection optical fiber is positioned; the incidence angle is determined by this fiber, through the two cited reflections. The thickness of the sensor head is such that it does not limit the outlet beam of the incident optical fiber. Between the detection optical fiber and the sensor head, a polarizer which only selects light with polarization p is placed.

Thus, the object of this patent, is to avoid the inconveniences of the discrete devices made up to now, making a small portable sensor device, without moveable pieces and which by means of optical fibers permits centralized remote control thereof.

In order to complement the description that is going to be made hereinafter and for the purpose of providing a better understanding of the features of the invention, the present specification is accompanied by a set of diagrams in whose figures the most significant details of the invention are represented.

BRIEF DESCRIPTION OF THE DESIGNS

FIG. 1—It shows a block diagram of the device.

FIG. 2—It shows a diagram of the sensor head and the relative position of the optical fibers in terms of the same.

FIG. 3—It shows a theoretical curve of the variation of the reflection coefficient.

FIG. 4—It shows some experimental measurements.

DESCRIPTION OF A PREFERRED EMBODIMENT

Figure 1:
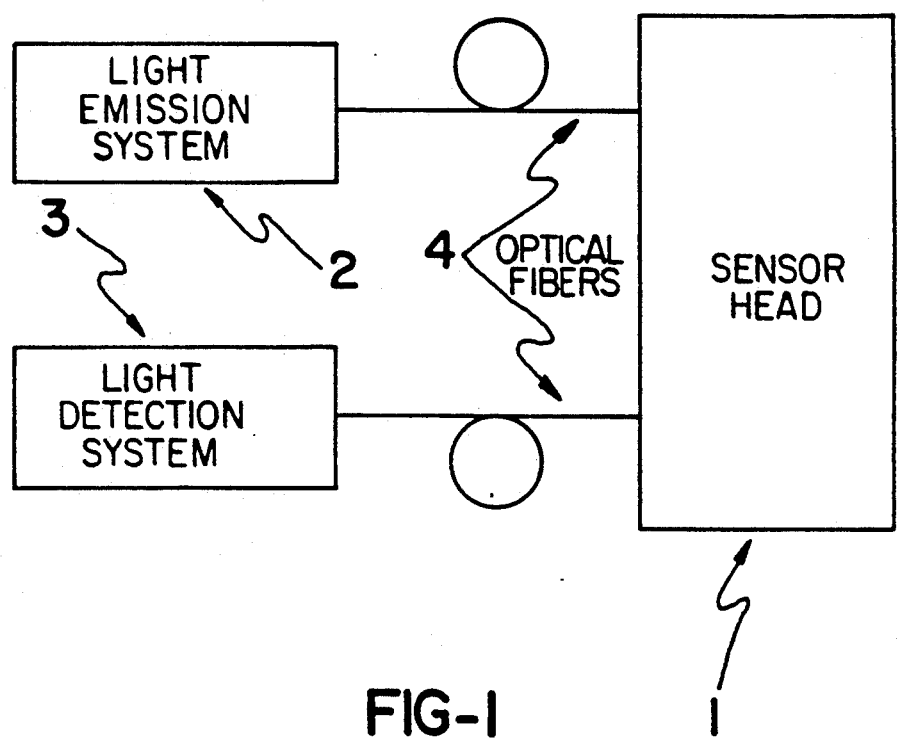
Figure 2:
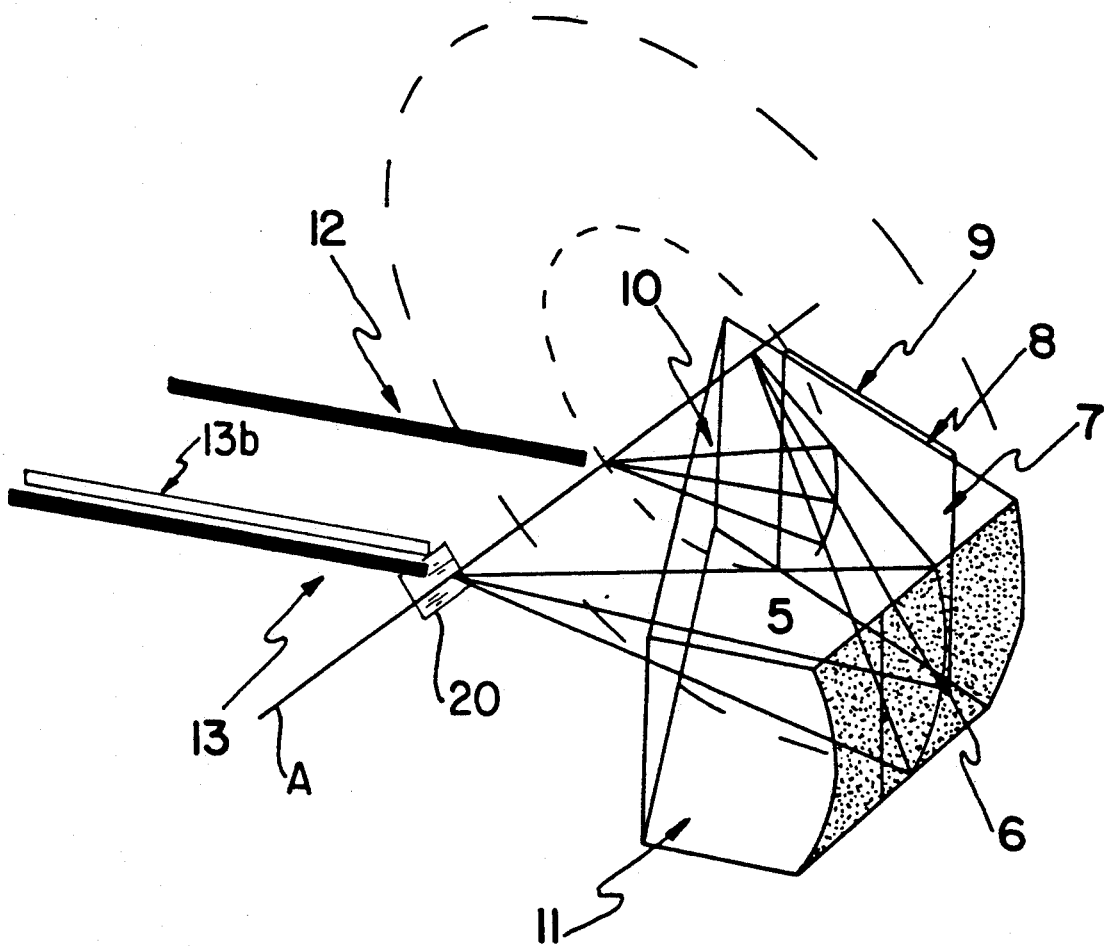

In view of the commented figures and in accordance with the numbering used, we can observe how the device of the invention is comprised of a sensor head (1), a light emission (2) and light detection (3) system and an optical fiber system (4) that connects the sensor head with the light emission and light detection systems.

The sensor head consists of a transparent geometric figure (5) in which one of its surfaces (6) is a cylindric mirror, whose axis A is in the plane of the geometric figure; upon the flat surface (7) and perpendicular to the cylindric mirror, a flat-parallel sheet (8) of a transparent material, such as glass or plastic, similar to that forming the geometric figure (5) and upon which a thin metal layer (9) has been deposited is adhered by means of a refractive index adapter liquid (for example, for BK7 glass, the B.P.X. "8711" adapter of DIFCO, n=1.532.) Upon this metal layer, for example, a layer of gold with a thickness between 25 nm and 60 nm, the optical excitation of surface plasmon is produced. Surface (10) forms with surface (7) an Φ angle which depends on the refractive index of the material, constituting the geometric figure (5) and the refractive index of the medium to be controlled. Surface (11) is parallel to surface (7).

The end of the incident optical fiber (12) is situated in the axis of the cylindric mirror (6), in such a way that the image of the end of the fiber through the metal film (9) and the cylindric mirror (6) is an interval of the axis itself of the cylinder. The metal film (9) can be gold, silver, aluminum, copper, platinum, palladium, titanium, tungsten or any other metal. In a point of this interval, the end of the detection optical fiber (13) is positioned; the incidence angle is determined by this fiber, through the two cited reflection. The thickness of the geometric figure (5) is such that it does not limit the outlet beam of the incident optical fiber. Between the detection optical fiber or the incident optical fiber and the sensor head, there is a polarizer 20 which only selects the light with polarization p.

With this geometric shape, the optimization of the photometric features of the device is obtained, permitting the use of the distribution of optical power in a distant field coming from the incident optical fiber entirely.

The optical fibers are connected to the sensor head by both connectors which can be of permanent or removeable connection. The types of optical fiber that can be used in this device are both multimode optical fibers, as well as monomode optical fibers, either of a high silica content or else of any other material (for example, plastic material).

The light emission system can use a LED (Luminiscent Electro Diode or Light Emission Diode) or a semiconductor laser emitting in any of the wave lengths used in optical fiber transmission windows, in other words, around 850 nm, 1,300 nm or 1,550 nm. The detection system uses conventionally used detectors and amplifiers used in optical fiber transmission systems.

In this shape, the optical power transmitted through the detection optical fiber is a function of the refractive index of the outer medium in contact with the metal film.

Figure 3:
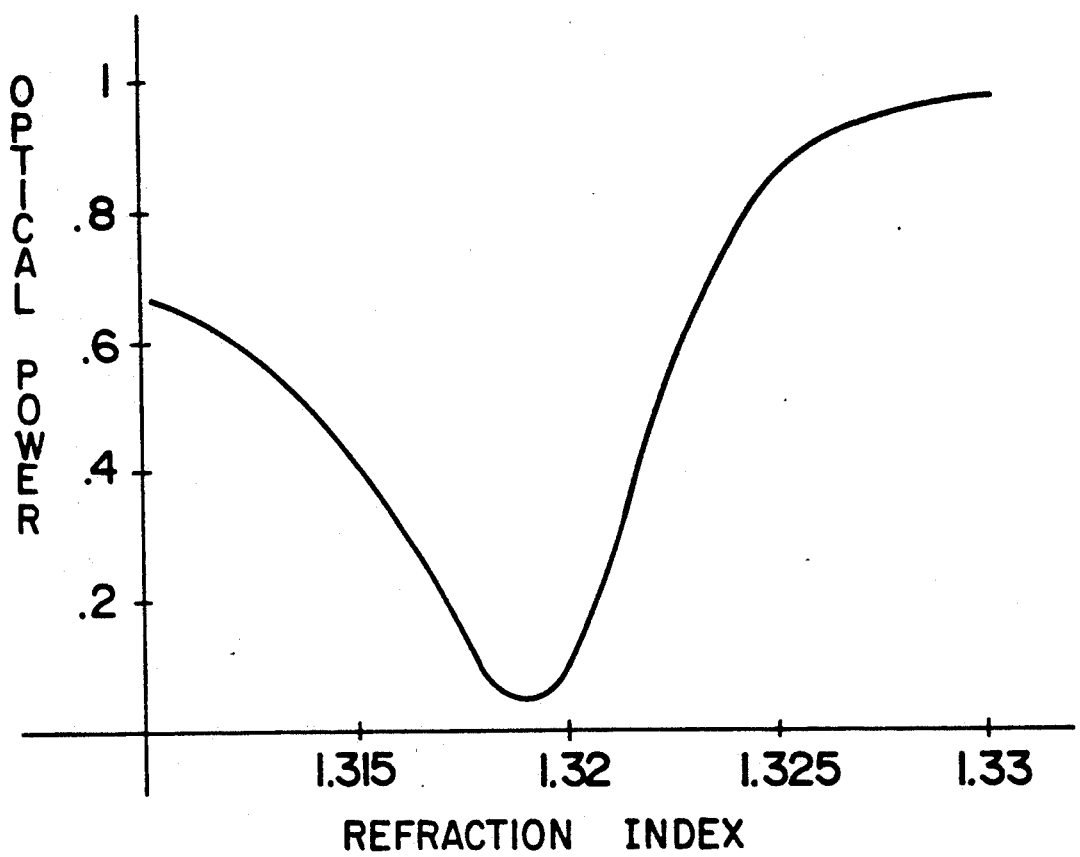

As an example, in FIG. 3, the standardized theoretical value of the optical power measured in terms of the refractive index of the outer medium, is shown. The position of the detection optical fiber is used only to select the operating point of the sensor head.

Figure 4:
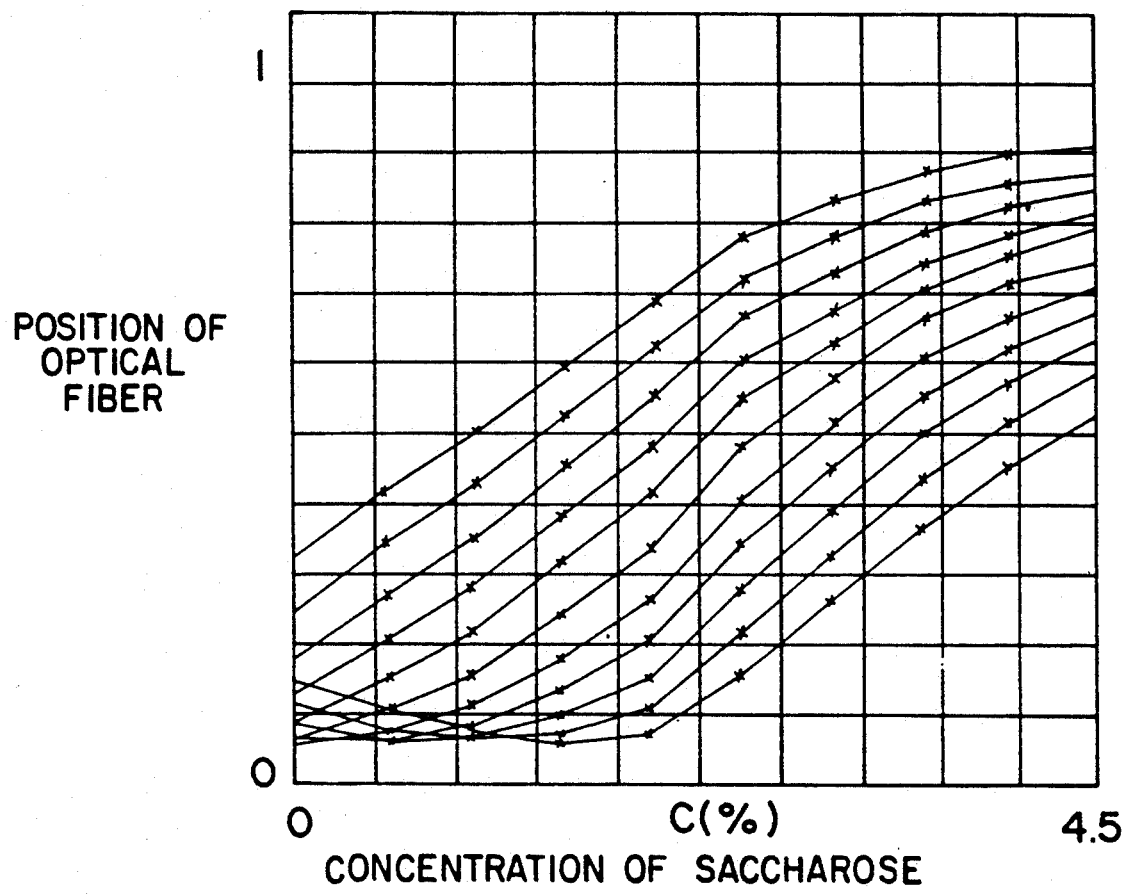

In FIG. 4 the results obtained for different positions of the detection optical fiber are given, in the measuring of the concentration of saccharose in an aqueous solution.

The sensor device can be provided with a dynamic self-gaging signal by placing another optical fiber 136 next to the detection optical fiber with the polarizer selecting the polarization s and therefore providing a reference signal, or else using as an outlet optical fiber a maintained polarization fiber; in this case, the polarizer is not required, since both polarizations are separated in the propagation through the fiber itself and they can be obtained individually in the detection stage.

In general, the sensor device can be used in multiple uses, in the field of chemistry or biochemistry, to detect species that are present in liquid or gas solutions. For uses in biosensors or in selective detection, the metal film can be coated with layers that cover the metal film with layers that include immobilized compounds, specifically sensitive to the species to be detected (for example enzymes and coenzymes, antigens and antibodies, etc.)

The sensitivity and dynamic range of the sensor can be optimized for the specific use of the same, coating the metal film with a transparent dielectric material, with adequate refractive index and thickness. Besides, this layer is also a protection against outer physical and chemical agents which can harm or affect the performance of the sensor.

Although the sensor has been oriented towards chemical or biochemical uses, it may also be used as an optical sensor to detect the variation of any physical or chemical parameter, which affects the optical properties of the outer medium to be controlled.

We claim:

1. An optical fiber sensor in an external medium based on optical excitation of surface plasmon, comprising:
    a sensor head comprising a transparent body with a first flat surface, said first flat surface having an adjacent thin metal layer on which the optical excitation of surface plasmon is produced, a mirrored cylindrical surface, said cylindrical surface being positioned perpendicular to said first flat surface and said cylindrical surface having an axis, a second flat surface forming an angle Φ with said first flat surface, said angle being determined by the refractive indexes of said transparent body and of the external medium, and a third flat surface positioned parallel to said first flat surface;

a first optical fiber connected to means for emitting light to said transparent body; and a second optical fiber connected to means for detecting light reflected from said transparent body;

said first and second optical fibers being positioned adjacent said second flat surface and in said axis, whereby variations of the optical properties of the sensor may be determined by measuring changes in energy per unit time in the light detected by the light detecting means.

2. The optical fiber sensor according to claim 1 in which said thin metal layer can be selected from the group consisting of gold, silver, aluminum, copper, platinum, palladium, titanium, tungsten and any other metal.

3. The optical fiber sensor according to claim 1 in which said thin metal layer is adhered to a fourth flat surface, said fourth flat surface being adhered to said first flat surface by means of a refraction index adapter.

4. The optical fiber sensor according to claim 3 in which said fourth flat surface is formed of glass.

5. The optical fiber sensor according to claim 3 in which said fourth flat surface is formed of plastic.

6. The optical fiber sensor according claim 3 in which said metal layer is coated with a layer of a transparent material.

7. The optical fiber sensor according claim 3 in which said metal layer is coated with a layer of a biochemical compound.

8. The optical fiber sensor according to claim 1 in which said first and second optical fibers comprise multimode optical fibers.

9. The optical fiber sensor according to claim 1 in which said first and second optical fibers comprise monomode optical fibers.

10. The optical fiber sensor according to claim 1 further comprising optical fiber means for receiving a reference signal.

11. The optical fiber sensor according to claim 1 further comprising a polarizer positioned between one of said first and second optical fibers and said transparent body, said polarizer selecting light with polarization p.

12. The optical fiber sensor according to claim 10 further comprising a polarizer positioned between said optical fiber means and said transparent body, said polarizer selecting light with polarization s.

13. The optical fiber sensor according to claim 1 wherein the light emitting means comprises a light emission source composed of a LED laser emitting light radiation with a wave length selected from the group of 850 nm., 1,300 nm. and 1,550 nm.

* * * * *